(12) United States Patent
Hatoum et al.

(10) Patent No.: US 11,667,895 B2
(45) Date of Patent: Jun. 6, 2023

(54) METHODS AND DEVICES RELATED TO CONTROLLED DELIVERY OF PHAGES AS A THERANOSTIC TOOL

(71) Applicant: THE BOARD OF TRUSTEES OF THE UNIVERSITY OF ALABAMA, Tuscaloosa, AL (US)

(72) Inventors: Asma Hatoum, Northport, AL (US); Shreyas Rao, Tuscaloosa, AL (US)

(73) Assignee: THE BOARD OF TRUSTEES OF THE UNIVERSITY OF ALABAMA, Tuscaloosa, AL (US)

( * ) Notice: Subject to any disclaimer, the term of this patent is extended or adjusted under 35 U.S.C. 154(b) by 295 days.

(21) Appl. No.: 16/865,748

(22) Filed: May 4, 2020

(65) Prior Publication Data
US 2020/0354689 A1    Nov. 12, 2020

Related U.S. Application Data

(60) Provisional application No. 62/846,116, filed on May 10, 2019.

(51) Int. Cl.
*C12N 7/00*    (2006.01)
*C12N 9/24*    (2006.01)
*C12Q 1/70*    (2006.01)

(52) U.S. Cl.
CPC ............ *C12N 7/00* (2013.01); *C12N 9/2402* (2013.01); *C12Q 1/70* (2013.01); *C12N 2795/10121* (2013.01); *C12N 2795/10131* (2013.01); *C12N 2795/10143* (2013.01); *C12N 2795/10221* (2013.01); *C12N 2795/10231* (2013.01);

(Continued)

(58) Field of Classification Search
None
See application file for complete search history.

(56) References Cited

U.S. PATENT DOCUMENTS 7,196,180 B2   3/2007  Aeschlimann et al.
8,096,365 B2   1/2012  Baggs
8,846,865 B2   9/2014  Briers et al.
(Continued)

FOREIGN PATENT DOCUMENTS

EP   1620038       2/2006
GB   2295893 B     6/1996

OTHER PUBLICATIONS

Aguado BA, Caffe JR, Nanavati D, Rao SS, Bushnell GG, Azarin SM, Shea LD. Extracellular matrix mediators of metastatic cell colonization characterized using scaffold mimics of the pre-metastatic niche. Acta Biomater 2016;33:13-24.

(Continued)

*Primary Examiner* — Michelle S Horning
(74) *Attorney, Agent, or Firm* — Meunier Carlin & Curfman LLC

(57) ABSTRACT

Disclosed herein is an engineered bacteriophage comprising an indicator gene, wherein said indicator gene is an RNA aptamer or a green fluorescent protein (GFP) or GFP-like protein, and further wherein said indicator gene can indicate the presence of a microorganism, such as a bacterial infection. The engineered bacteriophage can be capable of infecting and killing the microorganism. The engineered microorganism can be in a composition for delivery to a subject, and can be in hyaluronic acid, for example. Also disclosed are methods of using the engineered bacteriophage to diagnose and/or treat a subject with a bacterial infection.

17 Claims, 7 Drawing Sheets

Figure 1:
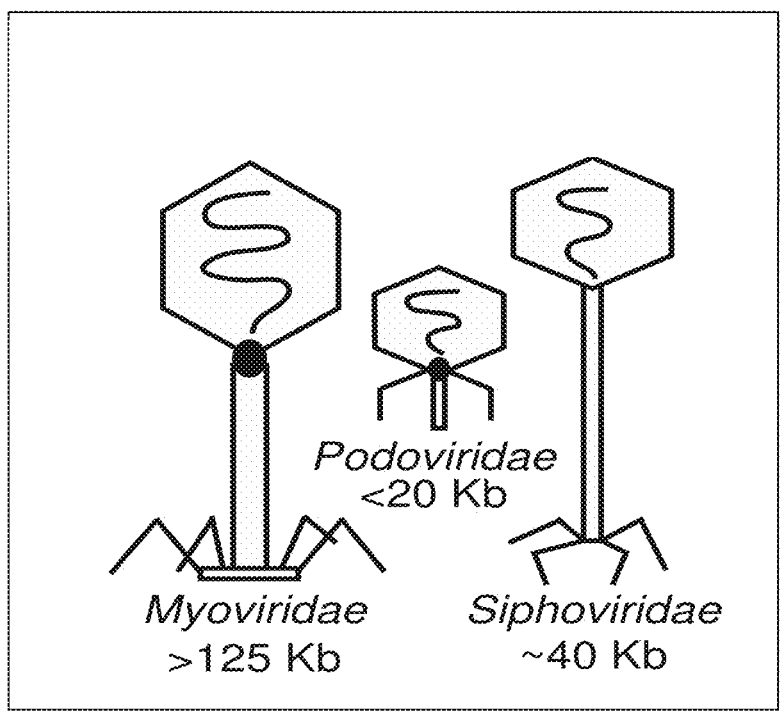

(52) U.S. Cl.
CPC ............... *C12N 2795/10243* (2013.01); *C12Y 302/01036* (2013.01)

(56) References Cited

U.S. PATENT DOCUMENTS

2010/0322903 A1    12/2010  Collins et al.
2015/0050717 A1    2/2015   Collins et al.

OTHER PUBLICATIONS

Aguado BA, Hartfield RM, Bushnell GG, Decker JT, Azarin SM, Nanavati D, Schipma MJ, Rao SS, Oakes RS, Zhang Y, Jeruss JS, Shea LD. Biomaterial Scaffolds as Pre-metastatic Niche Mimics Systemically Alter the Primary Tumor and Tumor Microenvironment. Adv Healthc Mater 2018;7:e1700903.
Ananthanarayanan B, Kim Y, Kumar S. Elucidating the mechanobiology of malignant brain tumors using a brain matrix-mimetic hyaluronic acid hydrogel platform. Biomaterials 2011;32:7913-23.
Antibiotic resistance threats in the United States. 2013, Centers for Disease Control and Prevention, Office of Infectious Disease.
Azarin SM, Yi J, Gower RM, Aguado BA, Sullivan ME, Goodman AG, Jiang EJ, Rao SS, Ren Y, Tucker SL, Backman V, Jeruss JS, Shea LD. In vivo capture and label-free detection of early metastatic cells. Nat Commun 2015;6:8094.
Bari SMN, Walker FC, Cater K, Aslan B, Hatoum-Aslan A. Strategies for Editing Virulent Staphylococcal Phages Using CRISPR-Cas10. ACS Synth Biol 2017;6:2316-25.
Bean JE, Alves DR, Laabei M, Esteban PP, Thet NT, Enright MC, Jenkins ATA. Triggered Release of Bacteriophage K from Agarose/Hyaluronan Hydrogel Matrixes by *Staphylococcus aureus* Virulence Factors. Chemistry of Materials 2014;26:7201-08.
Bean, Jessica Eleanor. Hydrogel Systems for Triggered Release of Bacteriophage K and Directed Cell Growth. Diss. University of Bath, 2015.
Borysowski J, Lobocka M, Miedzybrodzki R, Weber-Dabrowska B, Gorski A. Potential of Bacteriophages and Their Lysins in the Treatment of MRSA Current Status and Future Perspectives. Biodrugs 2011;25:347-55.
Bouhedda et al Light-Up RNA Aptamers and Their Cognate Fluorogens: From Their Development to Their Applications; Int. J. Mol. Sci. 2018, 19 44.
Briers, Yves, and Rob Lavigne. Breaking barriers: expansion of the use of endolysins as novel antibacterials against Gram-negative bacteria. Future microbiology 10.3 (2015): 377-390.
Briers, Yves, et al. Art-175 is a highly efficient antibacterial against multidrug-resistant strains and persisters of *Pseudomonas aeruginosa*. Antimicrobial agents and chemotherapy 58.7 (2014): 3774-3784.
Briers, Yves, et al. Engineered endolysin-based "Artilysins" to combat multidrug-resistant gram-negative pathogens. MBio 5.4 (2014).
Brussow H, Canchaya C, Hardt WD. Phages and the evolution of bacterial pathogens: From genomic rearrangements to lysogenic conversion. Microbiology and Molecular Biology Reviews 2004;68:560-602.
Caliendo AM, Gilbert DN, Ginocchio CC, Hanson KE, May L, Quinn TC, Tenover FC, Alland D, Blaschke AJ, Bonomo RA, Carroll KC, Ferraro MJ, Hirschhorn LR, Joseph WP, Karchmer T, MacIntyre AT, Reller LB, Jackson AF, Infectious Diseases Society of A. Better tests, better care: improved diagnostics for infectious diseases. Clin Infect Dis 2013;57 Suppl 3:S139-70.
Cater K, Dandu VS, Bari SM, Lackey K, Everett GF, Hatoum-Aslan A. A Novel *Staphylococcus podophage* Encodes a Unique Lysin with Unusual Modular Design. mSphere 2017;2.
Chen W, Palazzo A, Hennink WE, Kok RJ. Effect of Particle Size on Drug Loading and Release Kinetics of Gefitinib-Loaded PLGA Microspheres. Mol Pharm 2017;14:459-67.
Cogen AL, Yamasaki K, Sanchez KM, Dorschner RA, Lai Y, MacLeod DT, Torpey JW, Otto M, Nizet V, Kim JE, Gallo RL. Selective antimicrobial action is provided by phenol-soluble modulins derived from *Staphylococcus epidermidis*, a normal resident of the skin. J Invest Dermatol 2010;130:192-200.
Collins MN, Birkinshaw C. Hyaluronic acid based scaffolds for tissue engineering—A review. Carbohydrate Polymers 2013;92:1262-79.
Cooper CJ, Mirzaei MK, Nilsson AS. Adapting Drug Approval Pathways for Bacteriophage-Based Therapeutics. Frontiers in Microbiology 2016;7, 1-15.
Damodarasamy M, Johnson RS, Bentov I, MacCoss MJ, Vernon RB, Reed MJ. Hyaluronan enhances wound repair and increases collagen III in aged dermal wounds. Wound Repair and Regeneration 2014;22:521-26.
Deghorain M, Van Melderen L. The Staphylococci phages family: an overview. Viruses 2012;4:3316-35.
Ferguson EL, Roberts JL, Moseley R, Griffiths PC, Thomas DW. Evaluation of the physical and biological properties of hyaluronan and hyaluronan fragments. Int J Pharm 2011;420:84-92.
Flores CO, Meyer JR, Valverde S, Farr L, Weitz JS. Statistical structure of host-phage interactions. Proc Natl Acad Sci USA 2011;108:E288-97.
Frenkel JS. The role of hyaluronan in wound healing. Int Wound J 2014;11:159-63.
Furuya EY, Lowy FD. Antimicrobial-resistant bacteria in the community setting. Nat Rev Microbiol 2006;4:36-45.
Grice EA, Segre JA. The skin microbiome. Nat Rev Microbiol 2011;9:244-53.
Hart ME, Hart MJ, Roop AJ. Genotypic and Phenotypic Assessment of Hyaluronidase among Type Strains of a Select Group of Staphylococcal Species. Int J Microbiol 2009;2009:614371.
Hathaway H, Milo S, Sutton JM, Jenkins TA. Recent advances in therapeutic delivery systems of bacteriophage and bacteriophage-encoded endolysins. Ther Deliv 2017;8:543-56.
Hatoum-Aslan A. Phage Genetic Engineering Using CRISPR(-)Cas Systems. Viruses 2018;1-11.
Hynes WL, Walton SL. Hyaluronidases of Gram-positive bacteria. Fems Microbiology Letters 2000;183:201-7.
Iwase T, Uehara Y, Shinji H, Tajima A, Seo H, Takada K, Agata T, Mizunoe Y. Staphylococcus epidermidis Esp inhibits *Staphylococcus aureus* biofilm formation and nasal colonization. Nature 2010;465:346-9.
Knopf-Marques H, Pravda M, Wolfova L, Velebny V, Schaaf P, Vrana NE, Lavalle P. Hyaluronic Acid and Its Derivatives in Coating and Delivery Systems: Applications in Tissue Engineering, Regenerative Medicine and Immunomodulation. Advanced Healthcare Materials 2016;5:2841-55.
Kobayashi T, Glatz M, Horiuchi K, Kawasaki H, Akiyama H, Kaplan DH, Kong HH, Amagai M, Nagao K. Dysbiosis and *Staphylococcus aureus* Colonization Drives Inflammation in Atopic Dermatitis. Immunity 2015;42:756-66.
Kugelberg E, Norstrom T, Petersen TK, Duvold T, Andersson DI, Hughes D. Establishment of a superficial skin infection model in mice by using *Staphylococcus aureus* and *Streptococcus pyogenes*. Antimicrob Agents Chemother 2005;49:3435-41.
Lai Y, Cogen AL, Radek KA, Park HJ, Macleod DT, Leichtle A, Ryan AF, Di Nardo A, Gallo RL. Activation of TLR2 by a small molecule produced by *Staphylococcus epidermidis* increases antimicrobial defense against bacterial skin infections. J Invest Dermatol 2010;130:2211-21.
Lukacik, Petra, et al. Structural engineering of a phage lysin that targets Gram-negative pathogens. Proceedings of the National Academy of Sciences 109.25 (2012): 9857-9862.
Marklein RA, Burdick JA. Spatially controlled hydrogel mechanics to modulate stem cell interactions. Soft Matter 2010;6:136-43.
McCall RL, Sirianni RW. PLGA nanoparticles formed by single- or double-emulsion with vitamin E-TPGS. J Vis Exp 2013:51015.
Naber CK. *Staphylococcus aureus* bacteremia: epidemiology, pathophysiology, and management strategies. Clin Infect Dis 2009;48 Suppl 4:S231-7.

(56) References Cited

OTHER PUBLICATIONS

Naik S, Bouladoux N, Linehan JL, Han SJ, Harrison OJ, Wilhelm C, Conlan S, Himmelfarb S, Byrd AL, Deming C, Quinones M, Brenchley JM, Kong HH, Tussiwand R, Murphy KM, Merad M, Segre JA, Belkaid Y. Commensal-dendritic-cell interaction specifies a unique protective skin immune signature. Nature 2015;520:104-8.

Narkhede AA, Crenshaw JH, Manning RM, Rao SS. The influence of matrix stiffness on the behavior of brain metastatic breast cancer cells in a biomimetic hyaluronic acid hydrogel platform. Journal of Biomedical Materials Research Part A 2018;106:1832-41.

Oh J, Byrd AL, Park M, Program NCS, Kong HH, Segre JA. Temporal Stability of the Human Skin Microbiome. Cell 2016;165:854-66.

Paige JS, Wu KY, Jaffrey Sr. RNA mimics of green fluorescent protein. Science 2011;333:642-6.

Pastagia M, Euler C, Chahales P, Fuentes-Duculan J, Krueger JG, Fischetti VA. A novel chimeric lysin shows superiority to mupirocin for skin decolonization of methicillin-resistant and -sensitive *Staphylococcus aureus* strains. Antimicrob Agents Chemother 2011;55:738-44.

Peacock SJ, de Silva I, Lowy FD. What determines nasal carriage of *Staphylococcus aureus*? Trends Microbiol 2001;9:605-10.

Philipson CW, Voegtly LJ, Lueder MR, Long KA, Rice GK, Frey KG, Biswas B, Cer RZ, Hamilton T, Bishop-Lilly KA. Characterizing Phage Genomes for Therapeutic Applications. Viruses-Basel 2018;10.

Pires et al. Genetically Engineered Phages: a Review of Advances over the Last Decade; Microbiol. Mol. Biol. Rev. Jun. 2016, 80 (3) 523-543.

Price RD, Myers S, Leigh IM, Navsaria HA. The role of hyaluronic acid in wound healing—Assessment of clinical evidence. American Journal of Clinical Dermatology 2005;6:393-402.

Rao SS, Bushnell GG, Azarin SM, Spicer G, Aguado BA, Stoehr JR, Jiang EJ, Backman V, Shea LD, Jeruss JS. Enhanced Survival with Implantable Scaffolds That Capture Metastatic Breast Cancer Cells In Vivo. Cancer Res 2016;76:5209-18.

Rao SS, DeJesus J, Short AR, Otero JJ, Sarkar A, Winter JO. Glioblastoma Behaviors in Three-Dimensional Collagen-Hyaluronan Composite Hydrogels. Acs Applied Materials & Interfaces 2013;5:9276-84.

Ryan EM, Gorman SP, Donnelly RF, Gilmore BF. Recent advances in bacteriophage therapy: how delivery routes, formulation, concentration and timing influence the success of phage therapy. Journal of Pharmacy and Pharmacology 2011;63:1253-64.

Sempertegui ND, Narkhede AA, Thomas V, Rao SS. A combined compression molding, heating, and leaching process for fabrication of micro-porous poly(epsilon-caprolactone) scaffolds. J Biomater Sci Polym Ed 2018:1-24.

Strack RL, Jaffrey SR. Live-cell imaging of mammalian RNAs with Spinach2. Methods Enzymol 2015;550:129-46.

Stryjewski ME, Chambers HF. Skin and soft-tissue infections caused by community-acquired methicillin-resistant *Staphylococcus aureus*. Clin Infect Dis 2008;46 Suppl 5:S368-77.

Tormo MA, Ferrer MD, Maiques E, Ubeda C, Selva L, Lasa I, Calvete JJ, Novick RP, Penades JR. *Staphylococcus aureus* pathogenicity island DNA is packaged in particles composed of phage proteins. Journal of Bacteriology 2008;190:2434-40.

Vandersteegen K, Mattheus W, Ceyssens PJ, Bilocq F, De Vos D, Pirnay JP, Noben JP, Merabishvili M, Lipinska U, Hermans K, Lavigne R. Microbiological and Molecular Assessment of Bacteriophage ISP for the Control of *Staphylococcus aureus*. Plos One 2011;6:e24418.

Voigt J, Driver VR. Hyaluronic acid derivatives and their healing effect on burns, epithelial surgical wounds, and chronic wounds: A systematic review and meta-analysis of randomized controlled trials. Wound Repair and Regeneration 2012;20:317-31.

Wigginton KR, Pecson BM, Sigstam T, Bosshard F, Kohn T. Virus inactivation mechanisms: impact of disinfectants on virus function and structural integrity. Environ Sci Technol 2012;46:12069-78.

Wittebole X, De Roock S, Opal SM. A historical overview of bacteriophage therapy as an alternative to antibiotics for the treatment of bacterial pathogens. Virulence 2014;5:226-35.

Xu et al. Hyaluronic Acid-Based Hydrogels: from a Natural Polysaccharide to Complex Networks. Soft Matter. 2012;8(12):3280-3294.

You M, Litke JL, Jaffrey SR. Imaging metabolite dynamics in living cells using a Spinach-based riboswitch. Proc Natl Acad Sci USA 2015;112:E2756-65.

FIGURE 3A-B

FIGURE 5A-B

METHODS AND DEVICES RELATED TO CONTROLLED DELIVERY OF PHAGES AS A THERANOSTIC TOOL

I. CROSS-REFERENCE TO RELATED APPLICATIONS

This application claims benefit of U.S. Provisional Application No. 62/846,116, filed May 10, 2019, incorporated herein by reference in its entirety.

II. BACKGROUND

*Staphylococcus* bacteria are dominant residents of the skin microbiome that have a range of opposing impacts on health and disease (Grice 2011; Oh 2016). *S. epidermidis* colonizes 100% of the human population and has been shown to promote human health by (i) preventing the colonization of *S. aureus* (Iwase 2010) (ii) producing antimicrobial peptides that target skin pathogens (Cogen 2010) and (iii) stimulating the human immune system to facilitate pathogen defense (Lai 2010; Naik 2015). In contrast, *S. aureus* asymptomatically colonizes 30% of the population and constitutes a major risk factor for recurrent invasive infections (Peacock 2001). *S. aureus* is a leading cause of skin and soft tissue infections (Grice 2011, Stryjewski 2008) bacteremia (Naber 2009) and has been implicated as a driver of atopic dermatitis disease progression (Kobayashi 2015). Pathogenic *S. aureus* strains that are resistant to all known antibiotics have recently emerged in both hospital and community settings (Naber 2009). The Center for Disease Control and Prevention (CDC) estimates drug-resistant *S. aureus* strains cause 80,461 severe infections and 11,285 deaths annually in the US alone (*Antibiotic resistance threats in the United States*. 2013, *Centers for Disease Control and Prevention, Office of Infectious Disease*). Therefore, developing "precision" antimicrobials that target specific *Staphylococcus* species is of primary importance to human health.

Bacterial viruses, also known as phages, are powerful antimicrobials that have been proposed as alternatives or supplements to conventional antibiotics (Wittebole 2014). Phages attach to a specific host, inject their DNA, and replicate exponentially until the host is eliminated. The high specificity of phages in attacking a single host or subset of related hosts within the same genus (Flores 2011) renders them ideal candidates for use as precision antimicrobials. Three morphological families of staphylococcal phages have been identified (FIG. 1) (Deghorian 2012). Of these, the majority of known isolates exhibit a temperate lifestyle that is unsuitable for antimicrobial applications. Temperate staphylococcal phages, which belong to the family Siphoviridae, integrate into the host genome and can promote pathogenicity through various mechanisms (Brussow 2004; Tormo 2008). In contrast, virulent staphylococcal phages, which belong to the families Myoviridae and Podoviridae, exhibit a swift replication cycle that destroys the host within minutes of infection. While virulent staphylococcal phages are optimal for antimicrobial applications (Borysowski 2011), over half their genes have undetermined functions, significantly elevating the concern for detrimental side-effects.

The dosage and timing of phage application are critical to the success of treatment (Ryan 2011), and thus, the optimal mechanism of phage delivery should have the built-in ability to modulate both of these variables. Hydrogels composed of hyaluronic acid (HA) have been extensively used for tissue engineering and drug delivery applications (Knopf-Marques 2016). Further, the utilization of HA is particularly beneficial as it is known to promote wound healing (Frenkel 2014; Ferguson 2011; Voight 2012; Price 2005; Damodarsamy 2014). Since *S. aureus* naturally produces the HA-degrading enzyme hyaluronidase (HAase) (Hart 2009), HA hydrogels provide an ideal substrate in which phages can be concentrated to high doses and released only in the presence of *S. aureus*. What is needed in the art is the successful implementation of whole-phage therapeutics, which requires both early detection of a mounting bacterial infection and prompt delivery of engineered minimal phages.

III. SUMMARY

Disclosed herein is an engineered bacteriophage comprising an indicator gene, wherein said indicator gene is an RNA aptamer, and further wherein said indicator gene can indicate presence of a target of interest. The RNA aptamer, such as Spinach or Mango aptamer, can cause fluorescence in presence of a corresponding molecule upon interaction with the said molecule. The corresponding molecule can be a GFP-like fluorophore, such as 3,5-difluoro-4-hydroxybenzylidene imidazolinone (DFHBI), 3,5-dimethoxy-4-hydroxybenzylidene imidazolinone (DMHBI), 4-dimethylaminobenzylidene imidazolinone (DMABI) or 2-hydroxybenzlidene imidazolinone (2-HBI). The bacteriophage can be a staphylococcal, clostridial, or streptococcal bacteriophage. For example, the bacteriophage can be specific for *Staphylococcus aureus, Streptococcus pneumoniae*, or *Clostridium difficile*, and can be capable of infecting and killing these bacterial strains. The engineered bacteriophages disclosed herein can be engineered to comprise a minimal number of genes.

Also disclosed herein is a composition comprising an engineered bacteriophage comprising an indicator gene, wherein said indicator gene is an RNA aptamer, and further wherein said indicator gene can indicate presence of a target of interest; and hyaluronic acid (HA), wherein said engineered bacteriophage is encapsulated within said HA. The HA can be crosslinked, either chemically or photo-crosslinked. The HA can form a hydrogel scaffold, which can allow for triggered release of the engineered bacteriophages upon contact with a target of interest. The HA hydrogel scaffold can have a pore size to facilitate triggered release of the engineered bacteriophage. The target of interest can be a specific bacterial species, such as *Staphylococcus aureus, Streptococcus pneumoniae*, or *Clostridium difficile*, and the engineered bacteriophage is capable of infecting and killing these targeted bacteria. The targeted bacteria can produce hyaluronidase (HAase), which can trigger release of the bacteriophage from the HA hydrogel. The RNA aptamer, such as Spinach or Mango aptamer, can cause fluorescence in presence of a corresponding molecule upon interaction with the said molecule. The corresponding molecule can be a GFP-like fluorophore, such as 3,5-difluoro-4-hydroxybenzylidene imidazolinone (DFHBI), 3,5-dimethoxy-4-hydroxybenzylidene imidazolinone (DMHBI), 4-dimethylaminobenzylidene imidazolinone (DMABI) or 2-hydroxybenzlidene imidazolinone (2-HBI). The HA can comprise a top layer encapsulating a polymer or a co-polymer particle, such as poly(lactic-co-glycolic acid) (PLGA), polylactide or poly(ε-caprolactone). The GFP-like fluorophores can be present in the polymer or co-polymer particle or in the HA top layer. The engineered bacteriophage can be engineered to comprise a minimal number of genes.

Also disclosed is a composition comprising: an engineered bacteriophage comprising an indicator gene, wherein said indicator gene can indicate presence of a target of interest; and hyaluronic acid (HA), wherein said engineered bacteriophage is encapsulated within said HA.

Further disclosed herein is a method for detecting presence of a target of interest, the method comprising: bringing into contact the composition comprising an engineered bacteriophage as described herein and the target of interest; and detecting interaction between the engineered bacteriophage and the target of interest, wherein said interaction indicates the presence of the target of interest.

Disclosed is a method of treating a subject in need thereof, the method comprising exposing the subject to the composition comprising an engineered bacteriophage described herein, and detecting interaction between the engineered bacteriophage and the specific bacterial species, wherein the engineered bacteriophage is infecting and killing the specific bacterial species while detection occurs. The subject can be a mammal, such as a human.

Further disclosed is a kit for treating a bacterial infection, the kit comprising a composition comprising an engineered bacteriophage as described herein. The composition can be provided in a patch, hydrogel pad, hydrogel dressing, hydrogel bandage, or wound dressing.

Also disclosed is a composition comprising an engineered bacteriophage directly encapsulated in hyaluronic acid (HA) using chemical- or photo-crosslinking.

IV. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows three morphological families of staphylococcal phages.

Figure 2:
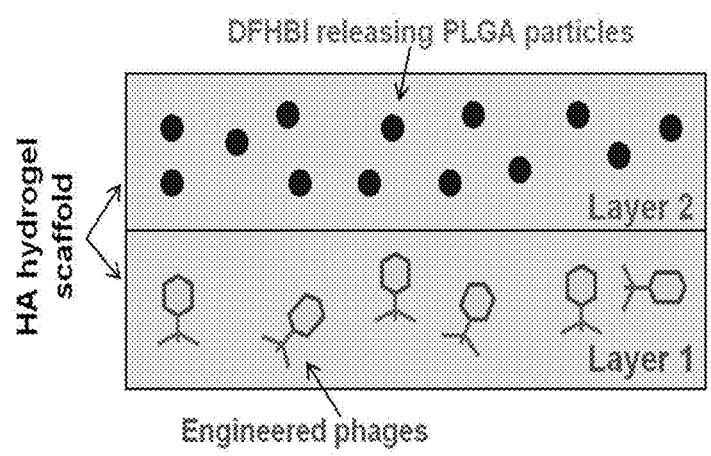

FIG. 2 shows a theranostic device for targeting *S. aureus*. HAase produced by *S. aureus* can enable release of engineered phages targeting *S. aureus* from layer 1. The engineered phages are equipped with mSpinach (a small RNA that fluoresces in the presence of 3,5-difluoro-4-hydroxybenzylidene imidazolinone (DFHBI)). These engineered phages express mSpinach only when actively replicating, thereby allowing their detection in the presence of DFHBI (released from PLGA (poly(lactic-co-glycolic acid)) particles in layer 2). Both layers are made of HA hydrogel scaffolds.

FIG. 3A-B shows transmission electron microscope (TEM) images of *Staphylococcus* phages Pabna (A) and ISP (B). Scale bar=100 nm.

Figure 4:
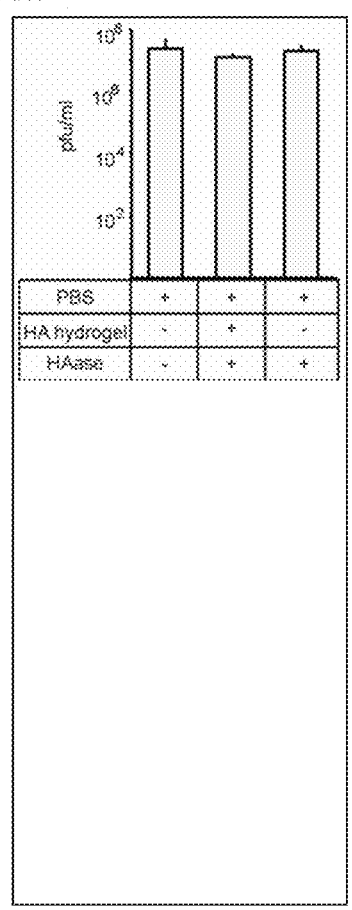

FIG. 4 shows phage viability in the HA hydrogel. Phages ($3 \times 10^7$ pfu/ml) were combined with the indicated component(s) in a 96-well plate and incubated at 37° C. for 4 hours. HAase (2000 U/mL) was then added to indicated wells, and the plate was allowed to continue incubation overnight. Phages were recovered from the wells and enumerated using a plaque assay. Shown is an average of plaque counts from triplicate wells +/−S.D.

Figure 5:
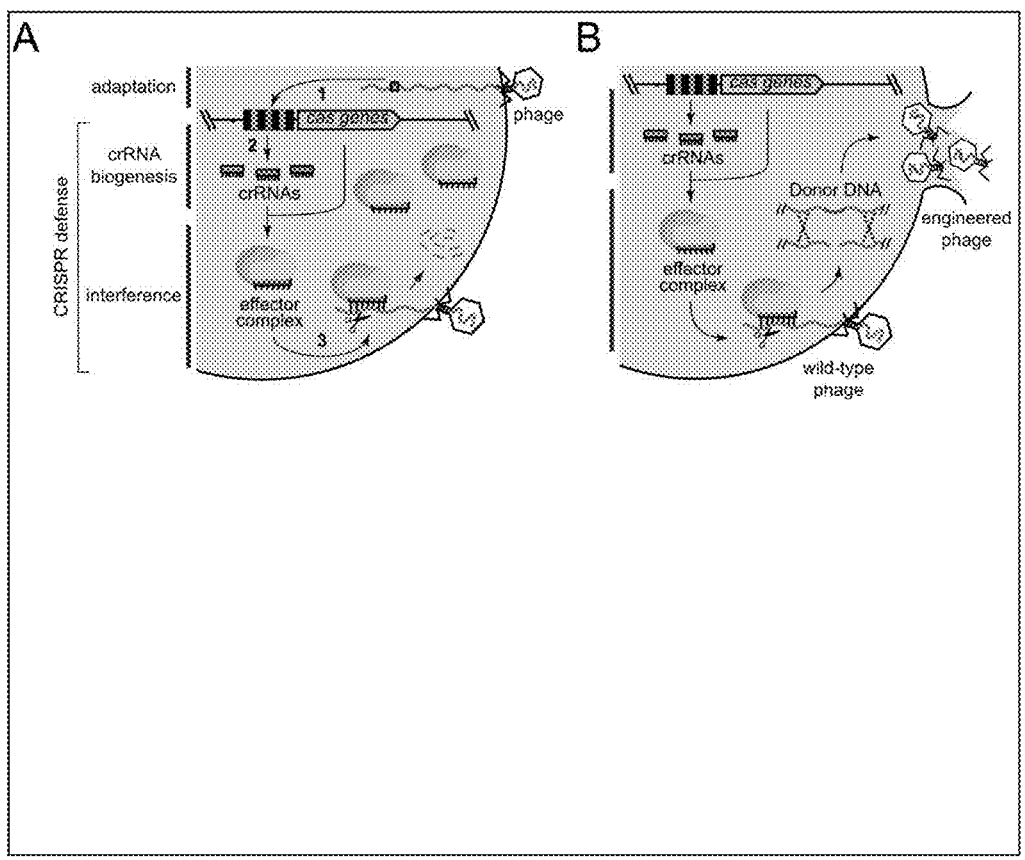

FIG. 5A-B depicts harnessing CRISPR-Cas immunity for phage engineering. (A) CRISPR-Cas immunity consists of three stages: (1) during adaptation, phage infection stimulates the incorporation of short (35-45 nucleotide) pieces of phage DNA into the CRISPR locus (colored rectangles), thus serving as "memories" of past invaders. (2) during crRNA biogenesis, the phage-derived DNA in the CRISPR locus is transcribed and the transcript is processed to generate mature crRNAs, each of which specifies the destruction of a different invader. The crRNAs combine with one or more Cas proteins to form an effector complex. (3) during interference, the effector complex detects and destroys nucleic acid invaders that match the sequence of the crRNA. (B) These systems can be harnessed to select for phages that have acquired desired mutations by programming the system to target the phage genome and providing a donor DNA construct containing desired mutations in the targeted region flanked by ~250 nucleotide sequences homologous to the phage genome. A bacterial strain containing the programmed CRISPR-Cas system and the donor DNA construct is termed the "editing strain". Phage editing is performed by plating phages on the editing strain—only those phages that recombine with the donor construct and take up the mutations will escape immunity and complete their replication cycle.

Figure 6:
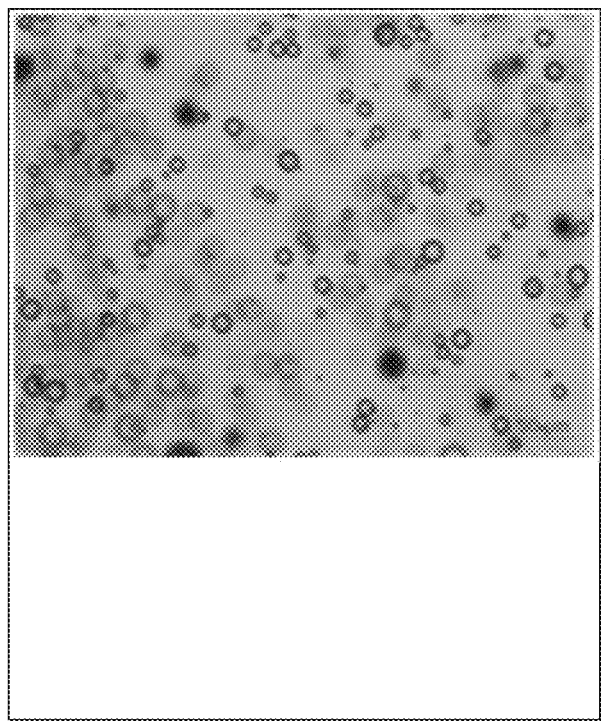

FIG. 6 shows optical microscopy image of PLGA particles. Scale bar=50 μm.

Figure 7:
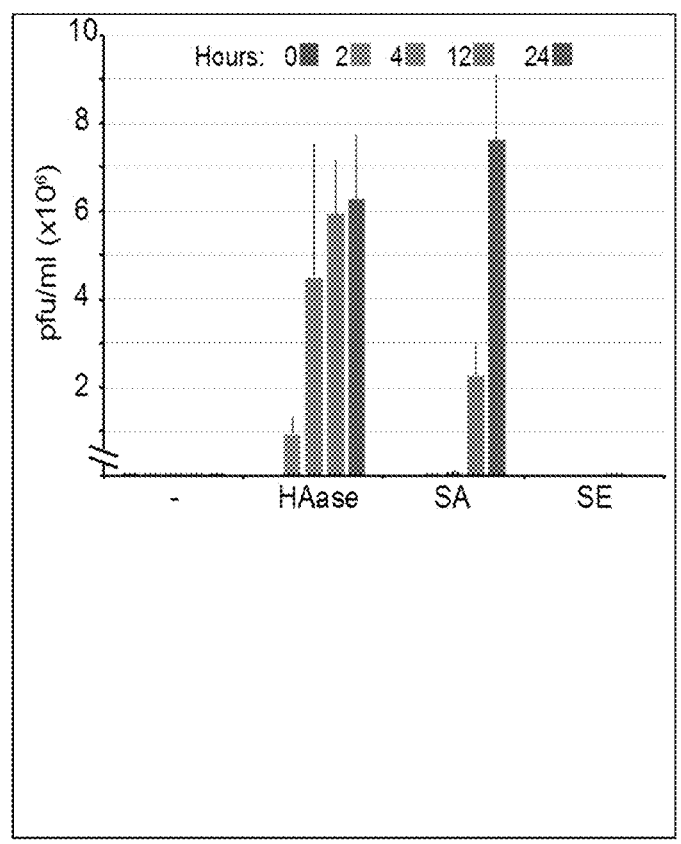

FIG. 7 shows phage ISP release kinetics from HA hydrogels after incubation with PBS (−), HAase (2000 U/mL), *S. aureus* (SA) supernatant, and *S. epidermidis* (SE) supernatant over a period of 24 h. Phages ($5.5 \times 10^9$ pfu/ml) were encapsulated in HA hydrogels in a 96-well plate and incubated at 37° C. At the indicated time points, 10 μL aliquots were removed to obtain phage titers and replenished with 10 μL of respective supernatants. Shown are average phage titers from triplicate wells +/−S.D.

V. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, a "subject" or "patient" or "individual" means a human or a non-human mammal, e.g., a dog, a cat, a mouse, a rat, a cow, a sheep, a pig, a goat, a non-human primate or a bird, (e.g., a chicken, a turkey, an ostrich, etc.) as well as any other vertebrate or invertebrate. The term "mammal" is used in its usual biological sense. Thus, it specifically includes humans, cattle, horses, dogs, and cats, but also includes many other species including, but not limited to, a llama, panda, lion, tiger, hippopotamus, rhinoceros, giraffe, rodent (e.g., mice, rats, rabbits, etc.), or a primate (e.g., monkeys, gorillas, chimpanzees, etc.) and all other forms including all Therians and Monotremes. In one embodiment, a mammal to be treated is a human.

As used herein, "bacteriophage" or "phage" includes one or more of a plurality of bacterial viruses. Bacteriophages are viruses that have evolved in nature to use bacteria as a means of replicating themselves. A phage does this by attaching itself to a bacterium and injecting its DNA (or RNA) into that bacterium and inducing it to replicate the phage hundreds or even thousands of times. This is referred to as phage amplification.

The term "colonization" as used herein refers to the process of a group of bacteria living together. It is further understood that "colonization" may or may not result in a pathological infection.

The term "microbial infection" as used herein refers to any pathological presence of at least one bacterial species on or in an injury or lesion to the skin of a human or animal. It is further understood that a "microbial infection" may include any systemic infection that is amenable to inhibition by application of the engineered bacteriophages of the present invention.

The term "medical dressing" as used herein refers to any covering, protective or supportive, for diseased or injured parts of the skin, or internal organs of a human or animal. The engineered bacteriophages disclosed herein can be present on any material applied to a wound. Optionally, the engineered bacteriophages can be contained in a hydrogel. The dressing comprising the hydrogel can be, but is not limited to, a patch, a bandage, or a wound covering of any kind known to those of skill in the art. The medical dressing as understood by the present invention may comprise a non-adherent dressing that will not adhere to an infected wound or injury, a protective dressing intended to prevent further injury or infection to the infected part of the body, and a wet dressing wherein the dressing is wetted before application to the infected site.

The term "burn" as used herein refers to tissue injury of the skin caused by thermal, chemical, or radiation exposure or abrasive friction. A burn may be a "first-degree burn" wherein there is superficial damage to the outer cornified layer, a "second-degree burn" wherein the damage extends down into the epidermal layer of cells but is not of sufficient extent that regeneration of the skin is prevented, or a "third-degree burn" wherein the injury extends below the dermis to the underlying tissue and wherein repair of the skin is not possible without grafting. The term "burn" as used herein also refers to any injury to the skin caused by an acid, an alkali, a brush or an abrasion, chemicals, electricity, explosive flash, hot liquids such as, but not only, boiling water, radiant energy such as heat, nuclear radiation or X-rays, or conductive thermal energy transfer due to direct contact with a hot surface or material. The term "burn" as used herein further refers to scalds due to exposure of the skin to hot liquids or gases that result in damage to the skin and underlying tissues.

The terms "lesion" and "surface lesion" as used herein refer to a circumscribed area of pathologically altered tissue, an injury or wound, or a single patch of a skin disease. The term "lesion" as used herein refers to primary lesions which are the immediate result of the pathological condition and may include, but are not limited to, cuts, abrasions, vesicles, blebs, bullae chancres, pustules, tubercles or any other such condition of the skin or a surface of the mouth, nose, anus or any other orifice of the body of a human or animal, or secondary lesions that later develop from a primary lesion and includes, but is not limited to, fissures and ulcers.

The term "ulcer" as used herein refers to an open sore or lesion of the skin or a mucous membrane that involves the sloughing off of inflamed and necrotized tissue and includes, but is not limited to, callous ulcers, chronic leg ulcers, decubitus, denture ulcers of the oral mucosa, traumatic ulcers of the mouth, infections stomatitis of the mouth and any type of secondary lesion that is a breach of the cornified and the epidermal layer of the skin.

The term "inhibiting the proliferation of a microbial population" as used herein refers to the bacteristatic or bacteriocidal activity of an antimicrobial composition, such as those engineered bacteriophages disclosed herein. The engineered bacteriophages described herein can prevent or treat bacterial infections caused by a microbial population. For example, the bacteriophages disclosed herein can reduce a microbial population by 10, 20, 30, 40, 50, 60, 70, 80, 90, or 100%, or any amount below or in between.

"Local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration but are undetectable or detectable at negligible amounts in distal parts of the subject's body. Administration includes self-administration and the administration by another.

"Biocompatible" generally refers to a material and any metabolites or degradation products thereof that are generally non-toxic to the recipient and do not cause significant adverse effects to the subject.

"Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention.

Embodiments defined by each of these transition terms are within the scope of this invention.

A "control" is an alternative subject or sample used in an experiment for comparison purposes. A control can be "positive" or "negative."

"Controlled release" or "sustained release" refers to release of an agent from a given dosage form in a controlled fashion in order to achieve the desired pharmacokinetic profile in vivo. An aspect of "controlled release" agent delivery is the ability to manipulate the formulation and/or dosage form in order to establish the desired kinetics of agent release.

"Pharmaceutically acceptable" component can refer to a component that is not biologically or otherwise undesirable, i.e., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., a non-immunogenic cancer). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. ENGINEERED BACTERIOPHAGES, COMPOSITIONS, METHODS OF USE

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular engineered bacteriophage comprising an indicator gene in a hydrogel is disclosed and discussed, and a number of modifications that can be made to the indicator gene as well as modifications to the hydrogel are discussed, specifically contemplated is each and every combination and permutation of the hydrogel and the indicator gene, unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

The evolution of antibiotic resistance in bacterial pathogens has ignited a renewed interest in exploring bacterial viruses (phages) as alternatives to conventional antibiotics. Drug-resistant *Staphylococcus aureus* poses a significant threat to human health worldwide (Tacconelli and Magrini, 2017). *S. aureus* is a leading cause of skin and soft tissue infections (Stryjewski and Chambers, 2008), and asymptomatic nasal carriage in ~30% of the population constitutes a major risk factor for recurrent infection (Peacock et al, 2001). Staphylococcal phages are useful as alternatives to conventional antibiotics (Borysowski et al, 2011). However, the dosage and timing of phage application are critical to the success of treatment (Ryan et al, 2011). In addition, the majority of phage genes have undetermined functions that can cause undesired downstream side-effects. This necessitates engineering of the phage genome to comprise the minimum number of genetic components required for bacterial destruction. In short, early detection of a mounting *S. aureus* infection and prompt eradication with phages that are genetically well-defined are crucial steps in the successful implementation of whole-phage therapeutics.

Disclosed herein is a system that utilizes bacteriophages to both detect and eliminate bacterial infections, such as *S. aureus*. This system utilizes engineered, genetically-compact phages, which can be released from a biocompatible hyaluronic acid (HA) hydrogel. HA is a natural polyanionic disaccharide that promotes wound healing (Park et al, 2017) and has broad applications in drug delivery and regenerative medicine (Rodrigues-Carmona and Villaverde, 2010). Since *S. aureus*, as well as other bacteria of interest, naturally produces the HA-degrading enzyme hyaluronidase (Hart et al, 2009), HA provides an ideal scaffold for localized and controlled phage delivery only in the presence *S. aureus* (or other specific bacterial species disclosed herein, such as *Streptococcus pneumoniae* and *Clostridium difficile*). CRISPR-Cas10 (Bari et al, 2017) can be used in a platform for genetic engineering of lytic staphylococcal phages. This system enables facile engineering of genetically compact, viable phages with dual diagnostic and antibiotic capabilities. A second HA hydrogel layer can be used to encapsulate the fluorophore required for fluorescence, although multiple layers are not required.

Engineered Bacteriophages

The engineered bacteriophage disclosed herein can comprise an indicator gene, wherein said indicator gene is an RNA aptamer, and further wherein said indicator gene can indicate the presence of a target of interest. The engineered bacteriophage, when exposed to a target of interest such as a bacteria, can signal its presence. This can be done via an RNA aptamer which has been engineered into the bacteriophage. RNA aptamers are well known in the art, such as the "light up aptamers" disclosed in Bouhedda et al (Light-Up RNA Aptamers and Their Cognate Fluorogens: From Their Development to Their Applications; *Int. J. Mol. Sci.* 2018, 19 44), which is incorporated by reference in its entirety for its teaching of RNA aptamers. A table from Bouhedda et al. is reproduced below, which includes various light-up aptamers, and their corresponding fluorogens:

The RNA aptamer causes fluorescence in the presence of a corresponding molecule (fluorophore) upon interaction with said molecule. The corresponding molecule can be, for example, a GFP-like fluorophore, such as 3,5-difluoro-4-hydroxybenzylidene imidazolinone (DFHBI), 3,5-dimethoxy-4-hydroxybenzylidene imidazolinone (DMHBI), 4-dimethylaminobenzylidene imidazolinone (DMABI) or 2-hydroxybenzlidene imidazolinone (2-HBI).

The bacteriophages disclosed herein can be specific for a certain bacteria or can be broadly specific for a class of bacteria (such as gram positive or gram negative). For example, the bacteriophage can be specific for *Enterococcus faecalis; Corynebacterium diphtheriae; Escherichia coli; Streptococcus coelicolor; Streptococcus pyogenes; Streptobacillus oniliformis; Streptococcus agalactiae; Streptococcus pneurmoniae; Salmonella typhi; Salmonella paratyphi; Salmonella schottmulleri; Salmonella hirshieldii; Staphylococcus epidermidis; Staphylococcus aureus; Klebsiella pzeumoniae; Legionella pneumophila; Helicobacter pylori; Mycoplasma pneumonia; Mycobacterium tuberculosis; Mycobacterium leprae; Yersinia enterocolitica; Yersinia pestis; Vibrio cholerae; Vibrio parahaemolyticus; Rickettsia prowozekii; Rickettsia rickettsii; Rickettsia akari; Clostridium difficile; Clostridium tetani; Clostridium perfringens; Clostridianz novyii; Clostridianz septicum; Clostridium botulinum; Legionella pneumophila; Hemophilus influenzue; Hemophilus parainfluenza; Hemophilus aegyptus; Chlamydia psittaci; Chlamydia trachonZatis; Bordetella pertcsis; Shigella* spp.; *Campylobacter jejuni; Proteus* spp.; *Citrobacter* spp.; *Enterobacter* spp.; *Pseudomonas aeruginosa; Propionibacterium* spp.; *Bacillus anthracis; Pseudomonas syringae; Spirrilum minus; Neisseria meningitidis; Listeria monocytogenes; Neisseria gonorrheae; Treponema pallidum; Francisella tularensis; Brucella* spp.; *Borrelia recurrentis; Borrelia hermsii; Borrelia turicatue; Borrelia burgdorferi; Mycobacterium avium; Mycobacterium smegmatis*; Methicillin-resistant *Staphyloccus aureus*; Vanomycin-resistant *enterococcus*; and multi-drug resistant bacteria (e.g., bacteria that are resistant to more than 1, more than 2, more than 3, or more than 4 different drugs).

TABLE 1

Main RNA-based fluorogenic modules and their properties.

| Fluorogen | Light-Up Aptamer | $K_D$ (nM) | Ex./Em. (nm) | $\varepsilon^1$ ($M^{-1}$/cm) | $\Phi^{complex\ 2}$ | Brightness[3] | Relative Brightness[4] | Ref. |
|---|---|---|---|---|---|---|---|---|
| GFP | / | / | 395/508 | 21,000 | 0.770 | 16.20 | 0.60 | (26) |
| eGFP | / | / | 490/508 | 39,200 | 0.680 | 26.60 | 1.00 | (26) |
| OTB | DiR2s-Apt | 662 | 380/421 | 73,000 | 0.510 | 37.23 | 1.40 | (27) |
| Hoescht | Apt II-mini3-4 c | 35 | 345/470 | n.a. | 0.260 | n.a. | n.a. | (28) |
| DFHB1 | Spinach | 540 | 469/501 | 24,300 | 0.720 | 17.50 | 0.65 | (29) |
| DFHBI-1T | Spinach2 | 560 | 482/505 | 31,000 | 0.940 | 29.10 | 1.10 | (30) |
| DFHBI-1T | Broccoli | 360 | 472/507 | 29,600 | 0.940 | 27.80 | 1.04 | (31) |
| DFHBI-2T | Spinach2 | 1300 | 500/523 | 29,000 | 0.120 | 3.48 | 0.10 | (30) |
| RG-DN | DNB | 4480 | 507/534 | 37,350 | 0.320 | 11.90 | 0.44 | (32) |
| TO-1 | Mango | 3 | 510/535 | 77,500 | 0.140 | 10.85 | 0.40 | (33) |
| DFHO | Corn | 70 | 505/545 | 29,000 | 0.250 | 7.25 | 0.27 | (34) |
| CY3-BHQ1 | BHQ apt (A1) | n.a. | 520/565 | n.a. | n.a. | n.a. | n.a. | (35) |
| DFHO | Red-Broccoli | 206 | 518/582 | 35,000 | 0.340 | 11.90 | 0.44 | (34) |
| TMR-DN | DNB | 350 | 555/582 | 47,150 | 0.900 | 42.43 | 1.60 | (32) |
| SR-DN | DNB | 800 | 572/391 | 50,250 | 0.980 | 49.24 | 1.80 | (32) |
| DIR | DIR apt | 56 | 600/646 | 134,000 | 0.260 | 34.8 | 1.30 | (36) |
| Mal. Green | MG aptamer | 117 | 630/650 | 150,000 | 0.187 | 28.00 | 1.05 | (19) |
| DIR-pro | DIR2s-Apt | 252 | 600/658 | 164,000 | 0.330 | 54.12 | 2.00 | (27) |
| T0-3 | Mango | 6-8 | 637/658 | 9300 | n.a. | n.a. | n.a. | (33) |
| Patent Blue | SRB apt | 23 | n.a./665 | n.a. | 0.034 | n.a. | n.a. | (19) |

Specifically, the bacteriophage can be a staphylococcal, clostridial, or streptococcal bacteriophage. For example, the bacteriophage can be specific for *Staphylococcus aureus*, *Streptococcus pneumoniae*, or *Clostridium difficile*, and can be capable of infecting and killing these bacterial strains.

The engineered bacteriophages disclosed herein can be engineered by means known in the art. For example, Pires et al. (Genetically Engineered Phages: a Review of Advances over the Last Decade; Microbiol. Mol. Biol. Rev. June 2016, 80 (3) 523-543) discloses multiple tools known in the art for engineering bacteriophages. For example, bacteriophages can be engineered using the CRISPR-Cas system. The CRISPR-Cas systems consist of two main components: the Cas proteins, which work as the catalytic core of the system and are responsible for cleaving DNA, and the CRISPR locus, which functions as the genetic memory that directs catalytic activity against foreign DNA. CRISPR loci are typically composed of several noncontiguous direct repeats separated by short stretches of variable DNA sequences, called spacers, acquired from extrachromosomal elements. Preferably, the bacteriophages disclosed herein can be edited to comprise a minimal number of genes.

Compositions Comprising Engineered Bacteriophages

The engineered bacteriophages disclosed herein can be encapsulated, so that they are released only upon contact with the proper substrate. For example, the engineered bacteriophages disclosed herein can be encapsulated in hyaluronic acid. *Staphylococcus aureus* is a primary cause of post-operative surgical site infection. *S. aureus*, as well as other known pathogens, produce hyaluronidase (HAase), which degrades hyaluronic acid (HA). This principal can be applied to treating wounds, as a desired antimicrobial can be encapsulated into hyaluronic acid. When the hyaluronic acid containing the antimicrobial (such as the engineered bacteriophages disclosed herein) is exposed to the pathogen producing HAase, the HA is broken down and the antimicrobial agent is released.

Therefore, disclosed herein is a composition comprising an engineered bacteriophage and hyaluronic acid (HA), wherein said engineered bacteriophage is encapsulated within said HA. As described above, the engineered bacteriophage can comprise an indicator gene, wherein said indicator gene is an RNA aptamer, and further wherein said indicator gene can indicate of a target of interest (such as pathogen like *S. aureus*). The engineered bacteriophage is released from HA upon contact with the pathogen, so that the engineered bacteriophage can then indicate the presence of the pathogen (as described below) as well as infect and kill the pathogen (also described below).

The HA can be crosslinked, either chemically or photo-crosslinked. For example, U.S. Pat. No. 7,196,180 (incorporated by reference herein for its teaching related to hyaluronic acid hydrogels) refers to methods for functionalization of hyaluronic acid and crosslinking thereof to form hydrogels. Xu et al. (Hyaluronic Acid-Based Hydrogels: from a Natural Polysaccharide to Complex Networks. Soft Matter. 2012; 8(12):3280-3294) disclose forming hydrogel scaffolds using HA (incorporated by reference for its teaching concerning hydrogel scaffolds). The hyaluronic acid derivatives can be crosslinked in situ by reaction with different functionalities or crosslinkers known to those of skill in the art, including photo and chemical cross-linking.

The cross-linking agent can be non-degradable, such as, without limitation, ethylene glycol diacrylate or dimethacrylate, 1,4-butylene dimethacrylate, diethylene glycol dimethacrylate, propylene glycol dimethacrylate, diethylene glycol dimethacrylate, dipropylene glycol dimethacrylate, diethylene glycol diacrylate, dipropylene glycol diacrylate, divinyl benzene, divinyltoluene, triallyl melamine, N,N'-methylene bisacrylamide, diallyl maleate, divinyl ether, diallyl monoethylene glycol citrate, vinyl allyl citrate, allyl vinyl maleate, divinyl sulfone, hexahydro-1,3,5-triallyltriazine, triallyl phosphite, diallyl benzene phosphonate, a polyester of maleic anhydride with triethylene glycol, diallyl aconitrate, divinyl citraconate, trimethylolpropane trimethacrylate and diallyl fumarate. Other non-degradable cross-linking agents will become apparent to those skilled in the art based on the disclosures herein and are within the scope of this invention. The HA can form a hydrogel scaffold, which allows for the triggered release of the engineered bacteriophages upon contact with a target of interest.

The HA hydrogel scaffold can have a pore size to facilitate triggered release of the engineered bacteriophage. For example, the pore size can range from 10-110 nm. Therefore, the pore size can be 10, 20, 30, 40, 50, 60, 70, 80, 90, 100, or 110 nm, or any amount in between. In one embodiment, the pore size is 50-100 nm.

In one embodiment, the hydrogel scaffold can comprise a top layer encapsulating a polymer or a co-polymer particle, such as poly(lactic-co-glycolic acid) (PLGA), polylactide or poly(ε-caprolactone). The fluorophores that correspond with the RNA aptamers described herein can be present in the polymer or co-polymer particle or in the HA top layer. In this manner, the presence of the target of interest (such as a pathogen, like *S. aureus*), can be detected. This occurs when an enzyme (such as HAase) of the target of interest breaks down the HA, thereby releasing the engineered bacteriophage comprising an RNA aptamer, which produces a fluorescent signal upon contact with the fluorophore contained in a layer of the HA hydrogel.

Methods for Detection and Treatment

Further disclosed herein is a method for detecting presence of a target of interest, the method comprising: bringing into contact the composition comprising an engineered bacteriophage as described herein and the target of interest; and detecting interaction between the engineered bacteriophage and the target of interest, wherein said interaction indicates the presence of the target of interest.

The engineered bacteriophage described herein can be used to detect the presence of a pathogen using an RNA aptamer engineered into the bacteriophage and a fluorophore contained in a hydrogel or other system that allows for its controlled release. Alternatively, the engineered bacteriophage can be used solely to treat a subject in need, without detecting the pathogen which is being infected and killed by the bacteriophage. Preferably, the engineered bacteriophage described herein can be used to both treat a subject infected with a pathogen, and to simultaneously detect the presence of the pathogen.

Phage therapy or viral phage therapy is the therapeutic use of bacteriophages to treat pathogenic bacterial infections. Bacteriophages invade bacterial cells and, in the case of lytic phages, disrupt bacterial metabolism and cause the bacterium to lyse. In addition to the natural bacteriocidal properties of bacteriophages, the engineered bacteriophages disclosed herein can be engineered to include other antimicrobial elements, such as an antimicrobial polypeptide. Exemplary antimicrobial peptides include, but are not limited to, Indolicidin, Cecropin PI, Dermaseptin, Ponericin WI, Ponericin W3, Ponericin W4, Ponericin W5, Ponericin W6, Maximin H5, Dermcidin, Andropin, Moricin, Cerototoxin, Melittin, Megainin, Bombinin, Brevinin, Esculentin, Buforin, CAP18, LL37, Abaecin, Prophenin, Protegrin, Tachyplesin, Defensin, Drosomycin, Apidaecin, Oncocin, or variants thereof. Additional antimicrobial peptides include those described in U.S. Patent Publication No. 2015/0050717, which is hereby incorporated by reference in its entirety.

In some embodiments, the antimicrobial polypeptide is a lytic enzyme, such as an endolysin, a lysozyme, a lysostaphin, or a functional derivative thereof. These enzymes range in size from 50 to several hundreds of amino acids and are predominantly used by bacteriophages and bacteria in inter- and intraspecies bacteriocidal warfare. In an embodiment, the enzymes induce the lysis of Gram-positive and/or Gram-negative bacteria. For example, the enzymes may effectively lyse one or more of *Staphylococcus aureus*, coagulase-negative staphylococci, streptococci, enterococci, anaerobes, and Gram-negative bacilli. Exemplary enzymes include, but are not limited to, Leeks, lysozyme, lysostaphin or a functional fragment thereof.

In some embodiments, the bacteriophage is engineered to comprise a nucleic acid encoding a chimera or fusion between the antimicrobial peptide and the lytic enzyme. In certain embodiments, the fusion or chimeric protein may induce the lysis of *Staphylococcus aureus* and/or other Gram-positive and Gram-negative bacteria. In an embodiment, the fusion or chimeric protein is particularly active against Gram-negative bacteria with an outer membrane. In an embodiment, the fusion or chimeric protein induces the lysis of *Staphylococcus aureus* which lacks an outer membrane as well as any neighboring Gram-negative bacteria. Exemplary chimeric or fusion proteins between an antimicrobial peptide and a lytic enzyme are described, for example, in U.S. Pat. Nos. 8,096,365 and 8,846,865, and Briers et al, (2015), Future Microbiol, 10(3): 377-90, Briers et al, (2014), Antimicrob Agents Chemother, 58(7): 3774-84, Briers et al, (2014), M. Bio, 5(4): e01379-14, and Lukacik et al, (2012), Proc Natl Acad Sci USA, 109(25): 9857-62, all of which are hereby incorporated by reference in their entireties.

In various embodiments, the bacteriophage is engineered to comprise a nucleic acid encoding an agent that potentiates antibiotic action, for example, by inhibiting the expression and/or function of an antibiotic resistance gene or a cell survival repair gene. Exemplary antibiotic resistance genes to target according to these embodiments are those that confer resistance to beta-lactams (e.g., methicillin) or vancomycin. Exemplary cell survival repair genes include *Staphylococcus* orthologs of recA, recB, recC, spoT or relA. Additional targets are disclosed, for example, in U.S. Patent Publication No. 2010/0322903, which is hereby incorporated by reference in its entirety. The expression or function of these genes may be targeted, for example, by expression of antisense polynucleotides, or double stranded RNA or other gene silencing techniques that are functional in the targeted host.

In various embodiments, the bacteriophage is engineered to comprise a nucleic acid encoding at least one gene that represses an SOS response gene and/or a non-SOS pathway bacterial defense gene. The SOS response in bacteria is an inducible DNA repair system, which allows bacteria to survive increased DNA damage. In some embodiments, the repressor is the *Staphylococcus* ortholog of lexA, or modified version thereof such as lexA3. In some embodiments, the gene represses SOS response genes such as marRAB, arcAB and lexO. Additional repressors are disclosed, for example, in U.S. Patent Publication No. 2010/0322903, which is hereby incorporated by reference in its entirety. In some embodiments, a repressor of a non-SOS pathway gene is one or more of soxR, marR, arc, fur, crp, icdA, craA, or ompA, or modified versions thereof. A non-SOS bacterial defense gene refers to genes expressed by a bacteria or a microorganism that serve to protect the bacteria or microorganism from cell death, for example, from being killed or growth suppressed by an antimicrobial agent.

In various embodiments, the bacteriophage is engineered to comprise a nucleic acid encoding an agent that increases the susceptibility of bacteria to an antimicrobial agent. In one embodiment, the agent increases the entry of an antimicrobial agent into a bacterial cell. Exemplary agents that increase the entry of an antimicrobial agent into a bacterial cell include, but are not limited to, genes encoding porin or porin-like proteins, such as OmpF, beta barrel porins, or other members of the outer membrane porin (OMP) functional superfamily. In another embodiment, the agent increases iron-sulfur clusters in the bacteria cell and/or increases oxidative stress or hydroxyl radicals in the bacteria. Examples of a susceptibility agent that increases the iron-sulfur clusters include agents that modulate (i.e. increase or decrease) the Fenton reaction to form hydroxyl radicals. Examples of agents that increase iron-sulfur clusters in the bacterial cell include, for example but not limited to genes encoding the proteins or homologues of IscA, IscR, IscS and IscU. Examples of agents which increase iron uptake and utilization include, for example but not limited to genes encoding the proteins or homologues of, EntC, ExbB, ExbD, Feci, FecR, FepB, FepC, Fes, FhuA, FhuB, FhuC, FhuF, NrdH, Nrdl, SodA and TonB. Additional agents that may increase the susceptibility of bacteria to an antimicrobial agent are disclosed, for example, in U.S. Patent Publication No. 2010/0322903, which is hereby incorporated by reference in its entirety.

The hyaluronic formulation encapsulating the engineered bacteriophage described herein can be provided in a patch, hydrogel pad, hydrogel dressing, hydrogel bandage, or wound dressing, for example.

In one example, the patch resembles a bandage. The adhesive tape can be clear so that the gel is visible. The gel can also be transparent, so the wound is visible as well. This allows a fluorescent signal to be detected. The patch is put together by first casting the gel with the phage inside. In one embodiment, the gel can be packaged inside a sealed package to prevent drying out. After removal from the package, the gel can be applied to the wound, and a separate piece of clear adhesive tape (optionally included with the kit) can be placed atop the gel to hold it in place.

A bacterial infection in a subject that may be treated by the methods, medical dressings and compositions of the present invention, may be any opportunistic infection by a bacterium, or a multiple infection of more than one species of bacteria, and wherein the proliferation of which can be inhibited by the application of the compositions and medical dressings of the present invention.

The methods disclosed herein can be used to treat infections or injuries to the skin which have, or may, become infected. These may be mechanical, such as an abrasion or cut, a burn from thermal, radiant or chemical exposure or a necrotic lesion of the surface tissue, or can be an ulcer. A break in the cornified layer or epidermis allows microorganisms to penetrate deep into the lower tissues and establish an infection that can spread throughout the body. A burn injury or other skin surface lesion exposes tissue on which a microorganism can thrive. The extent of the infection will depend on the severity or depth of the burn and the surface area affected.

The compositions comprising engineered bacteriophages described herein can be formulated as pharmaceutical compositions, e.g., can include a composition as described previously formulated with one or more pharmaceutically acceptable carriers or excipients. The pharmaceutical compositions are useful for wound healing in humans and other animals, such as mammals and birds. Such pharmaceutical compositions are known to those of skill in the art.

The engineered bacteriophages may be administered at once or may be administered at intervals of time. It is understood that the precise dosage and duration of treatment is a function of the wound and may be determined empirically using known testing protocols or by extrapolation from in vivo or in vitro test data. It is to be noted that concentrations and dosage values may also vary with the severity of the wound. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions. In some embodiments, the compositions are provided in unit dosage forms suitable for single administration, or multi-dose administration, of a precise dose.

Appropriate dosages and timing for wound healing can depend on the patient (species, age, weight, health), the severity of the wound, the type of formulation and other factors known to those having ordinary skill in the art. It is to be noted that concentrations and dosage values may vary with the severity of the wound. It is to be further understood that for any particular patient, specific dosage regimens should be adjusted over time according to the individual need and the professional judgment of the person administering or supervising the administration of the compositions.

The compositions comprising an engineered bacteriophage as described herein can also include an excipient. Excipients for use in the compositions described herein include any excipient for use in a composition that may be applied for therapeutic purposes. One or more excipients may comprise, for example, water, saline, Ringer's solution, dextrose, ethanol, glucose, sucrose, dextran, mannose, mannitol, sorbitol, polyethylene glycol (PEG), phosphate, acetate, gelatin, collagen, Carbopol®, vegetable oils, white petrolatum or a combination thereof.

Additional excipients include, but are not limited to, compounds that promote skin absorption, such as dimethyl sulfoxide (DMSO), partial glycerides of fatty acids, and the like, present at levels up to about 10 wt. % of the total formula weight. Examples of partial fatty acid glycerides include, but are not limited to IMWITOR 742 and IMWITOR 308 available from SASOL North America, Inc., of Houston, Tex. The topical formulations may also optionally include inactive ingredients to improve cosmetic acceptability, including but not limited to, humectants, surfactants, fragrances, coloring agents, emollients, fillers, and the like.

Compositions may also, in some instances, further comprise one or more suitable preservatives, stabilizers, antioxidants, antimicrobials, buffering agents, or a combination thereof.

Suitable preservatives include, but are not limited to, acids, alcohols, glycols, parabens, quaternary-nitrogen containing compounds, isothiazolinones, aldehyde-releasing compounds and halogenated compounds. In one embodiment, preservatives for use herein include, but are not limited to, imidazolidinyl urea, diazolidinyl urea, phenoxyethanol, methylparaben, ethylparaben, propylparaben, or a combination thereof. Additional examples of preservatives useful for the purpose of the present disclosure can be found in Steinberg, D. "Frequency of Use of Preservatives 2007". Cosmet. Toilet. 117, 41-44 (2002) and, "Preservative Encyclopedia" Cosmet. Toilet. 117, 80-96 (2002).

A wide variety of acids, bases, and buffers may be utilized to adjust and/or maintain the pH of the compositions useful in the present methods. Examples of materials useful for adjusting and/or maintaining the pH include, without limitation, phosphate, citrate, and other organic acids; ammonia, sodium carbonate, sodium hydroxide, triethanolamine, hydrochloric acid, phosphoric acid, sodium hydrogen phosphate, sodium dihydrogen phosphate, citric acid, and the like.

Suitable antioxidants for use herein include, but are not limited to, ascorbic acid and methionine.

Further disclosed is a kit for treating a bacterial infection, the kit comprising the composition comprising an engineered bacteriophage as described herein. The composition can be provided in a patch, hydrogel pad, hydrogel dressing, hydrogel bandage, or wound dressing. The kit can comprise all of the necessary components to treat/diagnose a subject in need thereof. The kit can therefore comprise the composition (which can be a hydrogel, patch, bandage, or dressing) in a sterile package, such as a plastic or foil package, that hermetically seals and protects the composition from degradation. The packaging can keep the composition sterile and moist. The kit can also comprise bandages or other items that are useful in treating or diagnosing a wound in a subject. For example, the kit can comprise a sterile wash, bandages, tape, or any other useful component. The kit can also comprise components useful in detecting an infection, such as a blacklight, microscope, or other detection device.

C. EXAMPLES

The following examples are put forth so as to provide those of ordinary skill in the art with a complete disclosure and description of how the compounds, compositions, articles, devices and/or methods claimed herein are made and evaluated and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Figure 3:
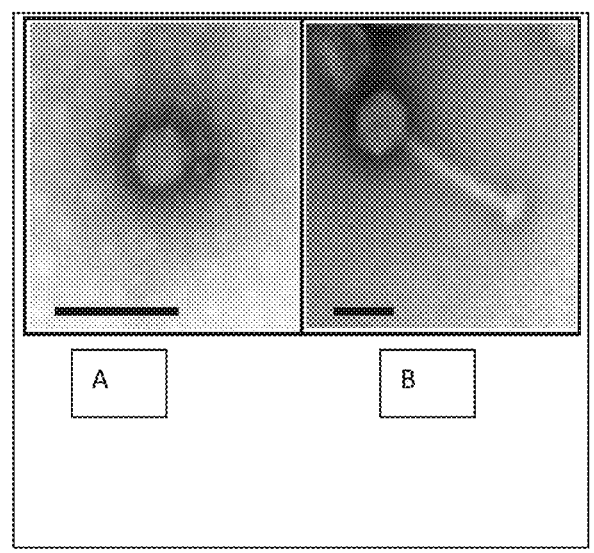

1. Example 1: Create and Optimize an HA Scaffold for Controlled Release of Wild-Type *S. aureus* Phages Although HA has been used as a 'barrier' layer for delivery of phages from agarose hydrogels (Bean 2014), phage-encapsulating HA hydrogels have not been reported. Disclosed herein is an optimized HA hydrogel scaffold that allows triggered release of wild-type phages. This optimized scaffold would essentially constitute Layer 1 of the device (FIG. 2). Representatives from both morphological families of lytic staphylococcal phages used as models: Myoviridae phage ISP (Vandersteegen 2011) and Podoviridae phage Pabna (FIG. 3). Phages will be encapsulated within HA hydrogels via chemical crosslinking. This process does not require UV light and is therefore advantageous to preserve phage viability.

Experimental Design and Methodology:

HA hydrogels are prepared using established procedures described previously (Ananthanarayanan 2011; Marklein 2010; Narkhede 2018). Briefly, HA-methacrylate is synthesized and then mixed with the cross linker DL-dithiothreitol (DTT) as well as the phages to create phage encapsulating hydrogels in situ at physiological conditions. Phages are encapsulated at a concentration of $3\times10^7$ pfu/mL (plaque-forming units per milliliter). HA hydrogels of varying formulations (i.e., mesh sizes) can be created by increasing the HA-methacrylate concentration or by changing the DTT concentration while keeping HA-methacrylate concentration constant (i.e., 5 wt %) to incorporate phages of varying sizes (FIG. 3). Swelling studies and mesh size estimation is performed as described previously (Narkhede 2018). Microstructural characterization will be performed using scanning electron microscopy (SEM). Mechanical characterization of hydrogels (compression testing) will be performed using the RSA-G2 Dynamic Mechanical Analyzer. Importantly, PI Rao has extensive experience with fabrication of HA-based hydrogels and their characterization (Narkhede 2018; Rao 2013).

To examine phage viability post encapsulation, they are isolated from hydrogels and plaque assays are performed using the double-agar overlay method as described previously (Cater 2017). Briefly, phages ($3\times10^7$ pfu/mL) encapsulated in HA hydrogels are retrieved by degrading the hydrogels with HAase (2000 U/mL) followed by homogenizing and repeatedly aspirating the mixture through an 18 gauge syringe needle. Samples are pelleted and the supernatant containing released phages are serially diluted and spotted atop a TSA (tryptic soy agar) plate containing the bacterial host in a second layer of soft agar. Plates are incubated overnight at 37° C. to allow bacteria and phage to replicate. On the following day, phage plaques (zones of clearing in the bacterial lawn) are enumerated. Results show that phage ISP remains viable when encapsulated in HA hydrogels crosslinked using 10 mM DTT (mesh size: 78±8.5 nm) (FIG. 4), thus underscoring the feasibility of these studies. For long term viability studies, phage encapsulating HA gels are incubated at 37° C. and retrieved at 1, 3, 7, 14, and 28 days post encapsulation, following which plaque assays are performed. For these studies, phage encapsulating HA gels are supplemented with PBS (phosphate buffered saline) or TSB (tryptic soy broth) to prevent dehydration.

Measuring phage release in the presence of HAase and bacterial supernatants: For triggered phage release studies, phage encapsulating HA hydrogels are incubated at 37° C. in varying HAase concentrations (0-2000 units/mL) as a control, or in bacterial supernatants from *S. aureus* and *S. epidermidis*. Aliquots of supernatant are taken at regular intervals over a period of 48 hours and replenished with an equal amount of fresh PBS, following which phages will be quantified as described above.

Testing the efficacy and specificity of phages released: To test efficacy, phage encapsulating HA hydrogels with optimal properties are prepared and placed onto a bacterial lawn of *S. aureus* for 12-16 hours. The zone of growth inhibition is then measured. To examine specificity, other skin-associated *Staphylococcus* species (such as *S. epidermidis*) are challenged with the phage encapsulating HA hydrogels. Efficacy of both phages (ISP and Pabna) are tested individually and in combination. The results show that phage ISP is released only in the presence of HAase and *S. aureus* ST398 supernatant but not in the presence of *S. epidermidis* RP62a supernatant (FIG. 7).

2. Example 2: Engineer Minimal Lytic Staphylococcal Phages with Diagnostic Capabilities The engineering of phages with minimal, well-defined genetic components is needed. In addition, eliminating genes that are not required for phage survival have the added benefit of creating space in the phage genome to encode additional capabilities, such as more potent antibacterial activity, expanded host range, and/or the ability to diagnose an infection. Compact ISP and Pabna variants that harbor the minimal genetic content required for phage replication can be created, and they can be built into these phages diagnostic capabilities using CRISPR-Cas10 assisted phage editing. CRISPR-Cas systems are a class of prokaryotic immune systems that use small CRISPR RNAs (crRNAs) in conjunction with one or more CRISPR-associated (Cas) proteins to detect and destroy invading phages (FIG. 5A). These systems can be harnessed as a mechanism to counter-select for phages that have acquired desired mutations from a donor DNA construct supplied in trans (FIG. 5B). Previously, a method to engineer staphylococcal phages using a Type III-A CRISPR-Cas system (also called CRISPR-Cas10) was developed, which is found in many staphylococci (Bari 2017). The engineered minimal phages disclosed herein serve as base genetic scaffolds into which diagnostic capability is built through the introduction of the mSpinach RNA aptamer (Paige 2011). mSpinach is a small RNA (<100 nucleotides) that binds the non-fluorescent small molecule 3,5-difluoro-4-hydroxybenzylidene imidazolinone (DFHBI) and switches it to a fluorescent state (Paige 2011; You 2015). The DFHBI can be presented in a second hydrogel layer. It is believed that when *S. aureus* is encountered, the engineered minimal phages encoding mSpinach initiate replication, producing the mSpinach RNA, and triggering DFHBI fluorescence.

Experimental Design and Methodology:

Identifying nonessential phage genes: Nonessential genes in phages Pabna and ISP are identified using a variation of the CRISPR-Cas10 phage editing approach. Briefly, editing strains that target each hypothetical gene (n=9 in Pabna and n=—150 in ISP) are created that contain two donor DNA constructs: one construct contains silent mutations in the targeted region, and a second construct contains premature stop codons. When the phage is cultured with this modified editing strain, it is presented with two possible solutions to escape CRISPR-Cas10 immunity—the acquisition of silent mutations or premature stop codons. Phages that replicate on this editing strain are purified and sequenced across the targeted region. The sequence of the targeted region reveals if the gene is essential: If 100% of edited phages incorporated the silent mutations, this indicates that the targeted gene is essential. Alternatively, if different proportions of phages incorporated the silent mutations and stop codons, this indicates the targeted gene is completely dispensable. Since CRISPR-Cas10 can eliminate 100% of wild-type phages, a relatively small number of phages would need to be screened (~10-20) to determine if stop codons can be incorporated. Genes that can harbor premature stop codons without compromising phage viability are deemed as nonessential. Due to its smaller size, Pabna is minimized first, followed by ISP.

Deleting nonessential phage genes: Once nonessential genes are systematically identified, they are deleted in order to make space for the insertion of additional capabilities using the CRISPR-Cas10 phage editing approach. Briefly, editing strains that target each nonessential gene identified in Pabna and ISP are created that contain a single donor DNA construct which harbors only the flanking regions of the gene to be deleted. Phages are propagated on this editing strain and survivors are purified and sequenced across the deletion region to confirm that the deletion was incorporated.

Introducing mSpinach RNA: A similar approach is used to insert the gene for mSpinach in place of one or more of the deleted genes in minimal phages. The donor construct is modified to include mSpinach and a strong promoter upstream of it in place of one or more deleted genes. These constructs are used in editing strains to insert these genetic elements into the minimal phage.

Testing intensity and specificity of fluorescence output by engineered phages: Once diagnostic phages are created, fluorescence output in the presence of DFHBI and specific *Staphylococcus* species is quantified. Briefly, phages ($3\times10^7$ pfu/mL) is combined with *S. aureus* or *S. epidermidis* cells in a 1:1 ratio in TSB plus DFHBI (20 μM) in a 96-well plate. Plates will be agitated and incubated at 37° C., and optical density at 600 nm (to detect cell growth) as well as fluorescence intensity under UV light will be measured every 30 min over the course of 12 h in a SpectraMax M2e microplate reader.

3. Example 3: An HA Scaffold that Immobilizes DFHBI to Enable *S. aureus* Detection In addition to the production of mSpinach RNA, the diagnostic capability of the disclosed device relies upon the presence of DFHBI. These composite biomaterial constructs are incorporated as an additional layer on top of the phage-releasing HA hydrogels (Layer 1). For layer 1, engineered minimal phages equipped with mSpinach are used which cause DFHBI to fluoresce. The effectiveness of these composite double-layer constructs to enable fluorescence based detection and targeting of *S. aureus* in vitro is measured.

Experimental Design and Methodology:

Preparing and characterizing polylactic-co-glycolic acid) PLGA microparticles encapsulating DFHB1: PLGA microspheres are prepared using established procedures (Chen 2017; Azarin 2015; McCall 2013). (FIG. 6). Briefly, a 6% (w/w) solution of PLGA (poly(D,L-lactide-co-glycolide) 75:25) in dicholormethane is prepared. DFHBI (molecular weight=252.22 g/mol) is dissolved in dimethyl sulfoxide (DMSO) at 10 mg/mL and is mixed with PLGA solution, and drop wise emulsified in a 2% poly(vinyl alcohol) solution while homogenizing the sample at ~10,000 rpm for 1-2 min. The solution is then be stirred overnight, following which the PLGA particles are collected via centrifugation, washed at least 3 times in deionized water, followed by lyophilization for 48 h. Blank particles without DFHBI are prepared as controls. PLGA particle sizes are characterized via SEM as well as optical microscopy. To determine encapsulation efficacy, PLGA particles encapsulating DFHBI is dissolved in DMSO, following which the mSpinach RNA (Eurofins Inc.) is used to activate DFHBI fluorescence and a standard curve is used to determine DFHBI concentration.

Measuring DFHBI release kinetics: DFHBI encapsulating PLGA microparticles are suspended in PBS and aliquots of supernatant taken at specific time points and replenished with equal amount of fresh PBS, followed by quantification utilizing mSpinach RNA to activate fluorescence. Release rates are measured from PLGA microparticles, as well as from PLGA microparticles encapsulated in HA hydrogels (Layer 2). In the latter scenario, varying concentrations of DFHBI-encapsulating PLGA microparticles are encapsulated in the hydrogel to determine an optimal formulation that enables fluorescence in the presence of mSpinach RNA. As a control, PLGA particles with no DFHBI is tested.

Detecting therapeutic specificity, efficacy, and sensitivity: Hydrogels are prepared and placed onto a bacterial lawn of *S. aureus* or *S. epidermidis* for 12-16 h, following which the zone of inhibition is measured. In parallel, gels are imaged in the presence of UV light. To determine detection sensitivity, hydrogels with varying phage particle counts ($10^3$-$10^8$ pfu/mL) are used. The following constructs are tested: (a) empty double layer hydrogels (b) double layer hydrogels with only phages in layer 1 (c) double layer hydrogels with only PLGA microparticles encapsulating DFHBI in layer 2 (d) double layer hydrogels with phages in layer 1 and PLGA microparticles encapsulating DFHBI in layer 2 (FIG. 2) and (e) no treatment.

Statistical analysis: Each condition is examined in triplicate, and independently repeated at least thrice. Multiple comparisons for various parameters (pfu/ml, fluorescence intensity, diameters of zones of inhibition, etc.) is performed using one-way ANOVA (JMP). Comparisons post ANOVA is performed using the Tukey-HSD test. If the data deviates markedly from a normal distribution, comparison is performed using the non-parametric Wilcoxon rank-sum test (for two samples) and the Steel-Dwass test (for multiple samples). To ensure robust and unbiased results, persons analyzing the results are blinded to the experimental groups.

4. Example 4: Test the Double-Layer Hydrogel Theranostic in a Mouse Skin Infection Model Introduction and Justification:

The optimized double layer hydrogel matrix is tested in vivo to validate the results observed in vitro. For these studies, a well-established mouse skin infection model is utilized, specifically, the tape stripping model (Pastiglia 2011; Kugelberg 2005). In this model, the skin is shaved and tape stripped using autoclave tape, followed by inoculation with bacteria. For our studies, both male and female (6-8 week) immune competent BALB/c mice are used. The efficacy of *S. aureus* detection by the matrix is determined, in addition to its ability to reduce colony counts and promote healthy tissue regeneration.

Experimental Design and Methodology:

Animal studies are performed with at least 6 mice/group with random assignment. For the procedure, mice are anaesthetized with Ketamine/Xylazine or isoflurane; following which, an area of ~2 $cm^2$ of the dorsum will be shaved using an electric razor. The shaved area is tape stripped ~20 times in succession using autoclave tape. The degree of irritation is standardized by measuring the trans epidermal water loss using a VapoMeter instrument. The tape stripped area is then inoculated with $10^7$ *S. aureus* cells harboring a gfp (green fluorescent protein) marker/5 μL in TSB as described (Pastagia 2011; Kugelberg 2005). Colonization of the infected area is verified by euthanizing mice at 24, 48, and 72 h post inoculation. Briefly, the infected skin area is excised, followed by homogenization of the tissue, and plating dilutions of this onto TSA plates. Bacterial colonies expressing gfp are counted at 24 h and 48 h post plating at 37° C.

The application of theranostic hydrogels to the infection site is performed 48 h post inoculation with bacterial cells. For this procedure, the animals are anesthetized as described above. Hydrogels are placed topically over the infection site followed by wrapping with Tegaderm™ and self-adhering elastic bandage (3M, Inc.). All materials are sterilized prior to use in mice. The following conditions are investigated: (a)

empty double layer hydrogels (b) double layer hydrogels with only phages in layer 1 (c) double layer hydrogels with only PLGA microparticles encapsulating DFHBI in layer 2 (d) double layer hydrogels with phages in layer 1 and PLGA microparticles encapsulating DFHBI in layer 2 (FIG. 2) (e) no treatment. An additional control group is included wherein the tape stripped area will not be inoculated with bacteria for imaging studies. To image the theranostic hydrogel, animals are anesthetized at day 2 and 4 post treatment with the hydrogels, the wrapping and bandage are carefully removed, and the images are taken under UV light followed by re-wrapping of the wounds. At 4 days post treatment, the infected area is excised, samples are homogenized, and the *S. aureus* colony-forming units (crus) are determined as described above. In parallel, 5 mm biopsy specimens are obtained from all experimental conditions for Hematoxylin and Eosin staining. In addition, Gram's crystal violet staining is performed to visualize bacteria.

D. REFERENCES

1. Grice E A, Segre J A. *The skin microbiome*. Nat Rev Microbiol 2011; 9:244-53.
2. Oh J, Byrd A L, Park M, Program NCS, Kong H H, Segre J A. *Temporal Stability of the Human Skin Microbiome*. Cell 2016; 165:854-66.
3. Iwase T, Uehara Y, Shinji H, Tajima A, Seo H, Takada K, Agata T, Mizunoe Y. *Staphylococcus epidermidis Esp inhibits Staphylococcus aureus biofilm formation and nasal colonization*. Nature 2010; 465:346-9.
4. Cogen A L, Yamasaki K, Sanchez K M, Dorschner R A, Lai Y, MacLeod D T, Torpey J W, Otto M, Nizet V, Kim J E, Gallo R L. *Selective antimicrobial action is provided by phenol-soluble modulins derived from Staphylococcus epidermidis, a normal resident of the skin*. J Invest Dermatol 2010; 130:192-200.
5. Lai Y, Cogen A L, Radek K A, Park H J, Macleod D T, Leichtle A, Ryan A F, Di Nardo A, Gallo R L. *Activation of TLR2 by a small molecule produced by Staphylococcus epidermidis increases antimicrobial defense against bacterial skin infections*. J Invest Dermatol 2010; 130:2211-21.
6. Naik S, Bouladoux N, Linehan J L, Han S J, Harrison O J, Wilhelm C, Conlan S, Himmelfarb S, Byrd A L, Deming C, Quinones M, Brenchley J M, Kong H H, Tussiwand R, Murphy K M, Merad M, Segre J A, Belkaid Y. *Commensal-dendritic-cell interaction specifies a unique protective skin immune signature*. Nature 2015; 520:104-8.
7. Peacock S J, de Silva I, Lowy F D. What determines nasal carriage of *Staphylococcus aureus*? Trends Microbiol 2001; 9:605-10.
8. Stryjewski M E, Chambers H F. *Skin and soft-tissue infections caused by community-acquired methicillin-resistant Staphylococcus aureus*. Clin Infect Dis 2008; 46 Suppl 5:S368-77.
9. Naber C K. *Staphylococcus aureus bacteremia: epidemiology, pathophysiology, and management strategies*. Clin Infect Dis 2009; 48 Suppl 4:S231-7.
10. Kobayashi T, Glatz M, Horiuchi K, Kawasaki H, Akiyama H, Kaplan D H, Kong H H, Amagai M, Nagao K. *Dysbiosis and Staphylococcus aureus Colonization Drives Inflammation in Atopic Dermatitis*. Immunity 2015; 42:756-66.
11. Furuya E Y, Lowy F D. *Antimicrobial-resistant bacteria in the community setting*. Nat Rev Microbiol 2006; 4:36-45.
12. Antibiotic resistance threats in the United States. 2013, Centers for Disease Control and Prevention, Office of Infectious Disease.
13. Wittebole X, De Roock S, Opal S M. *A historical overview of bacteriophage therapy as an alternative to antibiotics for the treatment of bacterial pathogens*. Virulence 2014; 5:226-35.
14. Flores C O, Meyer J R, Valverde S, Farr L, Weitz J S. *Statistical structure of host-phage interactions*. Proc Natl Acad Sci USA 2011; 108:E288-97.
15. Deghorain M, Van Melderen L. *The Staphylococci phages family: an overview*. Viruses 2012; 4:3316-35.
16. Brussow H, Canchaya C, Hardt W D. *Phages and the evolution of bacterial pathogens: From genomic rearrangements to lysogenic conversion*. Microbiology and Molecular Biology Reviews 2004; 68:560-602.
17. Tormo M A, Ferrer M D, Maiques E, Ubeda C, Selva L, Lasa I, Calvete J J, Novick R P, Penades J R. *Staphylococcus aureus pathogenicity island DNA is packaged in particles composed of phage proteins*. Journal of Bacteriology 2008; 190:2434-40.
18. Borysowski J, Lobocka M, Miedzybrodzki R, Weber-Dabrowska B, Gorski A. *Potential of Bacteriophages and Their Lysins in the Treatment of MRSA Current Status and Future Perspectives*. Biodrugs 2011; 25:347-55.
19. Cooper C J, Mirzaei M K, Nilsson A S. *Adapting Drug Approval Pathways for Bacteriophage-Based Therapeutics*. Frontiers in Microbiology 2016; 7.
20. Bari S M N, Walker F C, Cater K, Aslan B, Hatoum-Aslan A. *Strategies for Editing Virulent Staphylococcal Phages Using CRISPR-Cas10*. ACS Synth Biol 2017; 6:2316-25.
21. Ryan E M, Gorman S P, Donnelly R F, Gilmore B F. *Recent advances in bacteriophage therapy: how delivery routes, formulation, concentration and timing influence the success of phage therapy*. Journal of Pharmacy and Pharmacology 2011; 63:1253-64.
22. Knopf-Marques H, Pravda M, Wolfova L, Velebny V, Schaaf P, Vrana N E, Lavalle P. *Hyaluronic Acid and Its Derivatives in Coating and Delivery Systems: Applications in Tissue Engineering, Regenerative Medicine and Immunomodulation*. Advanced Healthcare Materials 2016; 5:2841-55.
23. Collins M N, Birkinshaw C. *Hyaluronic acid based scaffolds for tissue engineering—A review*. Carbohydrate Polymers 2013; 92:1262-79.
24. Frenkel J S. *The role of hyaluronan in wound healing*. Int Wound J 2014; 11:159-63.
25. Ferguson E L, Roberts J L, Moseley R, Griffiths P C, Thomas D W. *Evaluation of the physical and biological properties of hyaluronan and hyaluronan fragments*. Int J Pharm 2011; 420:84-92.
26. Voigt J, Driver V R. *Hyaluronic acid derivatives and their healing effect on burns, epithelial surgical wounds, and chronic wounds: A systematic review and meta-analysis of randomized controlled trials*. Wound Repair and Regeneration 2012; 20:317-31.
27. Price R D, Myers S, Leigh I M, Naysaria H A. *The role of hyaluronic acid in wound healing—Assessment of clinical evidence*. American Journal of Clinical Dermatology 2005; 6:393-402.
28. Damodarasamy M, Johnson R S, Bentov I, MacCoss M J, Vernon R B, Reed M J. *Hyaluronan enhances wound repair and increases collagen III in aged dermal wounds*. Wound Repair and Regeneration 2014; 22:521-26.

29. Hart M E, Hart M J, Roop A J. *Genotypic and Phenotypic Assessment of Hyaluronidase among Type Strains of a Select Group of Staphylococcal Species*. Int J Microbiol 2009; 2009:614371.
30. Hynes W L, Walton S L. *Hyaluronidases of Gram-positive bacteria*. Ferns Microbiology Letters 2000; 183: 201-07.
31. Caliendo A M, Gilbert D N, Ginocchio C C, Hanson K E, May L, Quinn T C, Tenover F C, Alland D, Blaschke A J, Bonomo R A, Carroll K C, Ferraro M J, Hirschhorn L R, Joseph W P, Karchmer T, MacIntyre A T, Reller L B, Jackson A F, Infectious Diseases Society of A. *Better tests, better care: improved diagnostics for infectious diseases*. Clin Infect Dis 2013; 57 Suppl 3:S139-70.
32. Bean J E, Alves D R, Laabei M, Esteban P P, Thet N T, Enright M C, Jenkins A T A. *Triggered Release of Bacteriophage K from Agarose/Hyaluronan Hydrogel Matrixes by Staphylococcus aureus Virulence Factors*. Chemistry of Materials 2014; 26:7201-08.
33. Wigginton K R, Pecson B M, Sigstam T, Bosshard F, Kohn T. *Virus inactivation mechanisms: impact of disinfectants on virus function and structural integrity*. Environ Sci Technol 2012; 46:12069-78.
34. Vandersteegen K, Mattheus W, Ceyssens P J, Bilocq F, De Vos D, Pirnay J P, Noben J P, Merabishvili M, Lipinska U, Hermans K, Lavigne R. *Microbiological and Molecular Assessment of Bacteriophage ISP for the Control of Staphylococcus aureus*. Plos One 2011; 6.
35. Ananthanarayanan B, Kim Y, Kumar S. *Elucidating the mechanobiology of malignant brain tumors using a brain matrix-mimetic hyaluronic acid hydrogel platform*. Biomaterials 2011; 32:7913-23.
36. Marklein R A, Burdick J A. *Spatially controlled hydrogel mechanics to modulate stem cell interactions*. Soft Matter 2010; 6:136-43.
37. Narkhede A A, Crenshaw J H, Manning R M, Rao S S. *The influence of matrix stiffness on the behavior of brain metastatic breast cancer cells in a biomimetic hyaluronic acid hydrogel platform*. Journal of Biomedical Materials Research Part A 2018; 106:1832-41.
38. Rao S S, DeJesus J, Short A R, Otero J J, Sarkar A, Winter J O. *Glioblastoma Behaviors in Three-Dimensional Collagen-Hyaluronan Composite Hydrogels*. Acs Applied Materials & Interfaces 2013; 5:9276-84.
39. Cater K, Dandu V S, Bari S M, Lackey K, Everett G F, Hatoum-Aslan A. *A Novel Staphylococcus Podophage Encodes a Unique Lysin with Unusual Modular Design*. mSphere 2017; 2.
40. Hathaway H, Milo S, Sutton J M, Jenkins T A. *Recent advances in therapeutic delivery systems of bacteriophage and bacteriophage-encoded endolysins*. Ther Deliv 2017; 8:543-56.
41. Philipson C W, Voegtly L J, Lueder M R, Long K A, Rice G K, Frey K G, Biswas B, Cer R Z, Hamilton T, Bishop-Lilly K A. *Characterizing Phage Genomes for Therapeutic Applications*. Viruses-Basel 2018; 10.
42. Hatoum-Aslan A. *Phage Genetic Engineering Using CRISPR(-)Cas Systems*. Viruses 2018; 10.
43. Paige J S, Wu K Y, Jaffrey S R. *RNA mimics of green fluorescent protein*. Science 2011; 333:642-6.
44. You M, Litke J L, Jaffrey S R. *Imaging metabolite dynamics in living cells using a Spinach-based riboswitch*. Proc Natl Acad Sci USA 2015; 112:E2756-65.
45. Chen W, Palazzo A, Hennink W E, Kok R J. *Effect of Particle Size on Drug Loading and Release Kinetics of Gefitinib-Loaded PLGA Microspheres*. Mol Pharm 2017; 14:459-67.
46. Azarin S M, Yi J, Gower R M, Aguado B A, Sullivan M E, Goodman A G, Jiang E J, Rao S S, Ren Y, Tucker S L, Backman V, Jeruss J S, Shea L D. *In vivo capture and label-free detection of early metastatic cells*. Nat Commun 2015; 6:8094.
47. McCall R L, Sirianni R W. *PLGA nanoparticles formed by single- or double-emulsion with vitamin E-TPGS*. J Vis Exp 2013:51015.
48. Aguado B A, Caffe J R, Nanavati D, Rao S S, Bushnell G G, Azarin S M, Shea L D. *Extracellular matrix mediators of metastatic cell colonization characterized using scaffold mimics of the pre-metastatic niche*. Acta Biomater 2016; 33:13-24.
49. Rao S S, Bushnell G G, Azarin S M, Spicer G, Aguado B A, Stoehr J R, Jiang E J, Backman V, Shea L D, Jeruss J S. *Enhanced Survival with Implantable Scaffolds That Capture Metastatic Breast Cancer Cells In Vivo*. Cancer Res 2016; 76:5209-18.
50. Sempertegui N D, Narkhede A A, Thomas V, Rao S S. *A combined compression molding, heating, and leaching process for fabrication of micro-porous poly(epsilon-caprolactone) scaffolds*. J Biomater Sci Polym Ed 2018: 1-24.
51. Strack R L, Jaffrey S R. *Live-cell imaging of mammalian RNAs with Spinach2*. Methods Enzymol 2015; 550:129-46.
52. Pastagia M, Euler C, Chahales P, Fuentes-Duculan J, Krueger J G, Fischetti V A. *A novel chimeric lysin shows superiority to mupirocin for skin decolonization of methicillin-resistant and -sensitive Staphylococcus aureus strains*. Antimicrob Agents Chemother 2011; 55:738-44.
53. Kugelberg E, Norstrom T, Petersen T K, Duvold T, Andersson D I, Hughes D. *Establishment of a superficial skin infection model in mice by using Staphylococcus aureus and Streptococcus pyogenes*. Antimicrob Agents Chemother 2005; 49:3435-41.
54. Aguado B A, Hartfield R M, Bushnell G G, Decker J T, Azarin S M, Nanavati D, Schipma M J, Rao S S, Oakes R S, Zhang Y, Jeruss J S, Shea L D. *Biomaterial Scaffolds as Pre-metastatic Niche Mimics Systemically Alter the Primary Tumor and Tumor Microenvironment*. Adv Healthc Mater 2018; 7:e1700903.

What is claimed is:

1. An engineered lytic staphylococcal bacteriophage comprising an indicator gene, wherein said indicator gene is an RNA aptamer, and further wherein said indicator gene can indicate a presence of a target of interest.

2. The engineered bacteriophage of claim 1, wherein said RNA aptamer can cause fluorescence in presence of a corresponding molecule upon interaction with the said molecule.

3. The engineered bacteriophage of claim 2, wherein said RNA aptamer is a Spinach aptamer or derivative thereof.

4. The engineered bacteriophage of claim 3, wherein the corresponding molecule is a green fluorescent protein (GFP) or GFP-like fluorophore.

5. The engineered bacteriophage of claim 4, wherein said GFP-like fluorophore is 3,5-difluoro-4-hydroxybenzylidene imidazolinone (DFHBI), 3,5-dimethoxy-4-hydroxybenzylidene imidazolinone (DMHBI), 4-dimethylaminobenzylidene imidazolinone (DMABI) or 2-hydroxybenzylidene imidazolinone (2-HBI).

6. The engineered bacteriophage of claim 1, wherein said engineered bacteriophage is capable of infecting and killing *Staphylococcus aureus*.

7. The engineered bacteriophage of claim 1, wherein said engineered bacteriophage has been engineered to comprise a minimal number of genes.

8. A composition comprising:
   a) an engineered lytic staphylococcal bacteriophage comprising an indicator gene, wherein said indicator gene is an RNA aptamer, and further wherein said indicator gene can indicate presence of a target of interest; and
   b) hyaluronic acid (HA), wherein said engineered bacteriophage is encapsulated within said HA.

9. The composition of claim 8, wherein said HA is crosslinked.

10. The composition of claim 9, wherein HA is chemically or photo-crosslinked.

11. The composition of claim 8, wherein said HA forms a hydrogel scaffold.

12. The composition of claim 11, wherein said HA hydrogel scaffold allows triggered release of the engineered bacteriophages upon contact with a target of interest.

13. The composition of claim 12, wherein said HA hydrogel scaffold has a pore size to facilitate triggered release of the engineered bacteriophage.

14. The composition of claim 8, wherein said target of interest is *Staphylococcus aureus*.

15. The composition of claim 14, wherein said bacteria produces hyaluronidase (HAase).

16. The composition of claim 8, wherein said RNA aptamer can cause fluorescence in presence of a corresponding molecule upon interaction with the said molecule.

17. A method for detecting presence of a target of interest, the method comprising:
   a. bringing into contact the composition of claim 8 and the target of interest; and
   b. detecting interaction between the engineered bacteriophage and the target of interest, wherein said interaction indicates the presence of the target of interest.

* * * * *